US012762551B2

(12) United States Patent
Jensen et al.

(10) Patent No.: US 12,762,551 B2
(45) Date of Patent: Oct. 13, 2026

(54) QUEUE MANAGEMENT SYSTEM

(71) Applicant: Medical Security Card Company, LLC, Tucson, AZ (US)

(72) Inventors: Jon Olaf Jensen, New Canaan, CT (US); Marcus Nicholas Sredzinski, Tucson, AZ (US); Brett Jeremy Masek, Tucson, AZ (US)

(73) Assignee: Medical Security Card Company, LLC, Tucson, AZ (US)

( * ) Notice: Subject to any disclaimer, the term of this patent is extended or adjusted under 35 U.S.C. 154(b) by 24 days.

(21) Appl. No.: 18/204,863

(22) Filed: Jun. 1, 2023

(65) Prior Publication Data

US 2024/0403872 A1 Dec. 5, 2024

(51) Int. Cl.

| | |
|---|---|
| ***G16H 20/10*** | (2018.01) |
| ***G06Q 20/20*** | (2012.01) |
| ***G06Q 20/38*** | (2012.01) |
| ***G16H 40/20*** | (2018.01) |
| ***G16H 70/40*** | (2018.01) |

(52) U.S. Cl.

CPC ......... *G06Q 20/387* (2013.01); *G06Q 20/202* (2013.01); *G16H 20/10* (2018.01); *G16H 40/20* (2018.01); *G16H 70/40* (2018.01)

(58) Field of Classification Search

CPC .... G06Q 20/387; G06Q 20/202; G16H 40/20; G16H 20/10; G16H 70/40

See application file for complete search history.

(56) References Cited

U.S. PATENT DOCUMENTS 8,712,797 B1 * 4/2014 Bezdek .............. G06Q 30/0639 705/400
2012/0185263 A1 * 7/2012 Emert .................... G16H 20/10 705/2
2014/0014720 A1 * 1/2014 Sarkis, Jr. .............. G16H 40/63 235/382
2014/0039911 A1 * 2/2014 Iyer .................... G06Q 30/0207 705/2
2014/0123209 A1 * 5/2014 Rajakarunanayake ...................... H04W 12/37 726/1
2019/0281558 A1 * 9/2019 Wu ....................... H04W 12/08
2021/0074401 A1 * 3/2021 Bezdek .................. G16H 10/60
2021/0313032 A1 * 10/2021 Fotsch ................ G06F 16/2471

* cited by examiner

*Primary Examiner* — Kambiz Abdi
*Assistant Examiner* — Kyra R Lagoy
(74) *Attorney, Agent, or Firm* — Procopio, Cory, Hargreaves & Savitch LLP; Pattric J. Rawlins

(57) ABSTRACT

A user system receives first information corresponding to a prescription drug purchase and obtains profile information corresponding to the prescription drug. The user system generates a plurality of queries, each query comprising at least a portion of the profile information, and sends each of the plurality of queries to one of a plurality of pharmacy discount services. The user system receives a response to each of the plurality of queries, each response including at least a discount price indicator for the prescription drug. The user system analyzes the responses and presents the results to facilitate a transaction to purchase the prescription drug at a discount.

19 Claims, 9 Drawing Sheets

This is an example computing device that we include to lay the physical groundwork for software implemented inventions because the software must execute in a hardware environement.

Search Page
On this page the user enters the name of the drug. Ideally this will be done by voice recognition, but if that does not work, the user can enter the drug name manually

500

600

Search Page
Includes keyboard for manual entry

700

QUEUE MANAGEMENT SYSTEM

BACKGROUND

Field of the Invention

The present disclosure is generally related to queue management and more particularly related to identification of options to improve transaction outcomes.

Related Art

Conventional commercial transactions are often significantly delayed by queue management failures. One particular queue management problem that delays commercial transactions is the search for and application of discounts to the commercial transaction. This delay is particularly significant in a convention prescription drug purchase transaction because many third party companies provide discounts and those discounts change in real time, which incentivizes consumers to review potential discounts from many third party companies before consummating the prescription drug purchase transaction. What is needed is a system and method that overcomes these significant problems found in the conventional commercial transactions as described above.

SUMMARY

Accordingly, described herein are solutions to the problems in the conventional commercial transactions described above. In some aspects, the techniques described herein relate to a system for increasing queue throughput, the system including: a user system configured to receive first information corresponding to a prescription drug purchase and obtain profile information corresponding to the prescription drug, the profile information including a plurality of first data elements including at least one of a brand name, a generic name, a drug form, one or more dosage amounts, and one or more quantity amounts, wherein the user system is further configured to, generate a plurality of queries, each query including at least a portion of the profile information, send each of the plurality of queries to one of a plurality of pharmacy discount services, receive a response to each of the plurality of queries, each response including second information including a plurality of second data elements including at least a discount price indicator for the prescription drug; a point of sale platform configured to receive third information corresponding to the prescription drug purchase and communicate with one or more external platforms to consummate a sale of the prescription drug, wherein the point of sale platform is further configured to provide at least a portion of the third information to the one or more external platforms in connection with the sale of the prescription drug, wherein the third information includes at least one of the first data elements and at least one of the second data elements.

In some aspects, the techniques described herein relate to an apparatus for increasing queue throughput, the system including: a cellular network communication system configured for data communication via a cellular network; a non-transitory computer readable medium configured to store executable programmed modules; a user interface configured to receive first information corresponding to a prescription drug purchase and present second information including at least a discount price indicator for the prescription drug purchase; a processor communicatively coupled with the non-transitory computer readable medium and configured to execute programmed modules stored in the non-transitory computer readable medium, the processor further configured to control the cellular network communication system to carry out data communication over the cellular network and to control the user interface to receive the first information and provide the second information; wherein the processor is further configured to, control the user interface to obtain profile information corresponding to the prescription drug, the profile information including a plurality of first data elements including at least one of a brand name, a generic name, a drug form, one or more dosage amounts, and one or more quantity amounts; generate a plurality of queries, each query including at least a portion of the profile information, send each of the plurality of queries to one of a plurality of pharmacy discount services, receive a response to each of the plurality of queries, each response including second information including a plurality of second data elements including at least a discount price indicator for the prescription drug; sort the responses to each of the plurality of queries by discount price indicators; and control the user interface to present the sorted list of responses to each of the plurality of queries.

In some aspects, the techniques described herein relate to a computer implemented method for increasing queue throughput, where one or more processors are programmed to perform steps including: control a user interface to obtain profile information corresponding to a purchase of a prescription drug, the profile information including a plurality of first data elements including at least one of a brand name of the prescription drug, a generic name of the prescription drug, a delivery form of the prescription drug, one or more dosage amounts of the prescription drug, and one or more quantity amounts of the prescription drug; generate a plurality of queries, each query including at least a portion of the profile information; send each of the plurality of queries to one of a plurality of pharmacy discount services; receive a response to each of the plurality of queries, each response including second information including a plurality of second data elements including at least a discount price indicator for the prescription drug; sort the responses to each of the plurality of queries based on the discount price indicators; and control the user interface to present the sorted list of responses to each of the plurality of queries.

In some aspects, the techniques described herein relate to a non-transitory computer readable medium having stored thereon one or more sequences of instructions for causing one or more processors to perform the steps for increasing queue throughput, the steps including: control a user interface to obtain profile information corresponding to a purchase of a prescription drug, the profile information including a plurality of first data elements including at least one of a brand name of the prescription drug, a generic name of the prescription drug, a delivery form of the prescription drug, one or more dosage amounts of the prescription drug, and one or more quantity amounts of the prescription drug; generate a plurality of queries, each query including at least a portion of the profile information; send each of the plurality of queries to one of a plurality of pharmacy discount services; receive a response to each of the plurality of queries, each response including second information including a plurality of second data elements including at least a discount price indicator for the prescription drug; sort the responses to each of the plurality of queries based on the discount price indicators; and control the user interface to present the sorted list of responses to each of the plurality of queries.

In some aspects, the techniques described herein relate to a system including at least one processor communicatively coupled with at least one non-transitory computer readable medium, wherein the processor is programmed to: control a user interface to obtain profile information corresponding to a purchase of a prescription drug, the profile information including a plurality of first data elements including at least one of a brand name of the prescription drug, a generic name of the prescription drug, a delivery form of the prescription drug, one or more dosage amounts of the prescription drug, and one or more quantity amounts of the prescription drug; generate a plurality of queries, each query including at least a portion of the profile information; send each of the plurality of queries to one of a plurality of pharmacy discount services; receive a response to each of the plurality of queries, each response including second information including a plurality of second data elements including at least a discount price indicator for the prescription drug; sort the responses to each of the plurality of queries based on the discount price indicators; and control the user interface to present the sorted list of responses to each of the plurality of queries.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Disclosed herein are systems, methods, and non-transitory computer-readable media for queue management. For example, one method disclosed herein allows for an apparatus to obtain prescription drug profile information corresponding to a proposed purchase of the prescription drug and send a query about the prescription drug to a plurality of pharmacy discount services. The apparatus subsequently receives a response to each of the queries and present a sorted list of the responses based on discount price indicators to facilitate purchase of the prescription drug using the discount information.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

1. System Overview

1.1. Infrastructure

Figure 1:
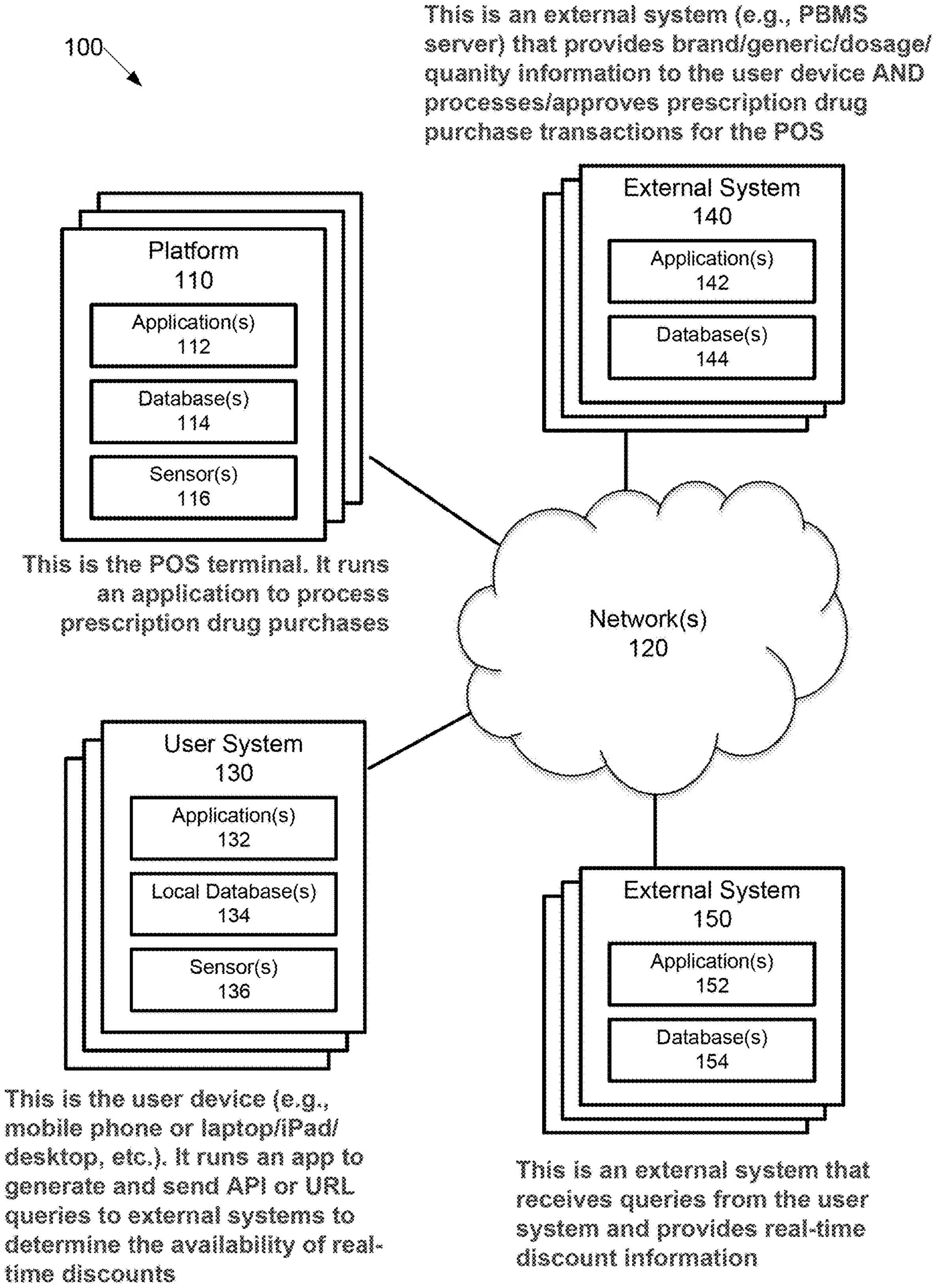
FIG. 1 illustrates an example infrastructure, in which one or more of the processes described herein may be implemented, according to an embodiment.

FIG. 1 illustrates an example infrastructure in which one or more of the disclosed processes may be implemented, according to an embodiment. The infrastructure may comprise a platform 110 (e.g., one or more servers or one or more point of sale (POS) devices) which hosts and/or executes one or more of the various functions, processes, methods, and/or software modules described herein. Platform 110 may comprise dedicated hardware and software, or may instead comprise cloud instances, which utilize shared resources of one or more servers. These POS devices, servers, and/or cloud instances may be collocated and/or geographically distributed. Platform 110 may also comprise or be communicatively connected to an application 112 and/or one or more databases 114. In addition, platform 110 may be communicatively connected to one or more user systems 130 via one or more networks 120. Platform 110 may also be communicatively connected to one or more external systems 140 and 150 (e.g., other platforms, websites, information repositories, databases, software-as-a-service platforms, etc.) via one or more networks 120.

Network(s) 120 may comprise a personal area network, a mesh network, a local area network, a wide area network, the Internet, and any combination of wired or wireless networks. Networks(s) 120 may also include direct wired or wireless connections such as Bluetooth®. Platform 110 may communicate with user system(s) 130 through the network 120 using standard transmission protocols, such as HyperText Transfer Protocol (HTTP), HTTP Secure (HTTPS), File Transfer Protocol (FTP), FTP Secure (FTPS), Secure Shell FTP (SFTP), and the like, as well as proprietary protocols. While platform 110 is illustrated as being connected to various systems through a single set of network(s) 120, it should be understood that platform 110 may be connected to the various systems via different sets of one or more networks. For example, platform 110 may be connected to a subset of user systems 130 and/or external systems 140 via the Internet, but may be connected to one or more other user systems 130 and/or external systems 140 via a private network such as an intranet or a direct communication link such as Bluetooth®. Furthermore, while only a few of each of the user systems 130, external systems 140, external systems 150, and platforms 110, are illustrated, it should be understood that the infrastructure may comprise any number of platforms, user systems, and external systems and any number of applications, databases, and sensors.

User system(s) 130 may comprise any type or types of computing devices capable of wired and/or wireless communication, including without limitation, desktop computers, laptop computers, tablet computers, smart phones or other mobile phones, servers, game consoles, head mounted displays, televisions, set-top boxes, electronic kiosks, point-of-sale terminals, Automated Teller Machines, and/or the like. In one aspect, user system 130 is a wireless communication device such as a smart phone that includes a sensor 136 such as a camera and the ability to communicate via a WIFI connection and also a cellular network connection.

External systems 140 and 150 may comprise web servers which host one or more websites and/or web services. In embodiments in which a website is provided, the website may comprise a graphical user interface, including, for example, one or more screens (e.g., webpages) generated in HyperText Markup Language (HTML) or other language. External systems 140 and 150 may also provide software-as-a-service capabilities and respond to queries that are received from, for example, platform 110 and/or user system 130. In doing so, external systems 140 and 150 may transmit or serve one or more screens of the graphical user interface in response to requests from platform 110 and/or user system(s) 130. In some embodiments, these screens may be served in the form of a wizard, in which case two or more screens may be served in a sequential manner, and one or more of the sequential screens may depend on an interaction of the user or user system 130 with one or more preceding screens. The requests to external systems 140 and 150 and the responses from external systems 140 and 150, including the screens of the graphical user interface, may both be communicated through network(s) 120, which may include the Internet, using standard communication protocols (e.g., HTTP, HTTPS, etc.). These screens (e.g., webpages) may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases (e.g., database(s) 144 and 154) that are locally and/or remotely accessible to external systems 140 and 150. External systems 140 and 150 may also respond to other requests from platform 110 and/or user system(s) 130.

Platform 110 may further comprise, be communicatively coupled with, or otherwise have access to one or more database(s) 114. For example, platform 110 may comprise one or more database servers which manage one or more databases 114. A user system 130 or application 112 executing on platform 110 may submit data (e.g., user data, form data, etc.) to be stored in database(s) 114, and/or request access to data stored in database(s) 114. Any suitable database may be utilized, including without limitation MySQL™, Oracle™, IBM™, Microsoft SQL™, Access™, PostgreSQL™, and the like, including cloud-based databases and proprietary databases. Data may be sent to platform 110, for instance, using the well-known POST request supported by HTTP, via FTP, and/or the like. This data, as well as other requests, may be handled, for example, by server-side web technology, such as a servlet or other software module (e.g., comprised in server application 112), executed by platform 110.

In embodiments in which a web service is provided, external systems 140 and 150 may receive requests from platform 110 and/or user system 130, and provide responses in extensible Markup Language (XML), JavaScript Object Notation (JSON), and/or any other suitable or desired format. In such embodiments, external systems 140 and 150 may provide an application programming interface (API) which defines the manner in which platform 110 and/or user system(s) 130 may interact with the web service. Thus, platform 110 and/or user system(s) 130, can define their own user interfaces, and rely on the web service to implement or otherwise provide the backend processes, methods, functionality, storage, and/or the like, described herein. For example, in such an embodiment, a client application 132 executing on one or more user system(s) 130 may interact with an application 142 or application 152 executing on external systems 140 and 150 to execute one or more or a portion of one or more of the various functions, processes, methods, and/or software modules described herein.

On the platform 110 and user system 130, application 112 and application 132 may be "thin," in which case processing is primarily carried out server-side by applications 142 or 152 on external systems 140 and 150. A basic example of a thin client application 112 and/or 132 is a browser application, which simply requests, receives, and renders webpages at platform 110 and/or user system(s) 130, while server applications 142 and/or 152 on external systems 140 and 150 are responsible for generating the webpages and managing database functions. Alternatively, the client application may be "thick," in which case processing is primarily carried out client-side by platform 110 or user system(s) 130. It should be understood that application 112 and/or application 132 may perform an amount of processing, relative to a server application 142 and/or 152 on external systems 140 and 150, at any point along this spectrum between "thin" and "thick," depending on the design goals of the particular implementation. In any case, the application described herein, which may wholly reside on user system(s) 130 or be distributed between platform 110 and user system(s) 130 (e.g., in which case application 112 and application 132 both perform processing), can comprise one or more executable software modules that implement one or more of the processes, methods, or functions of the application described herein.

1.2. Example Processing Device

Figure 2:
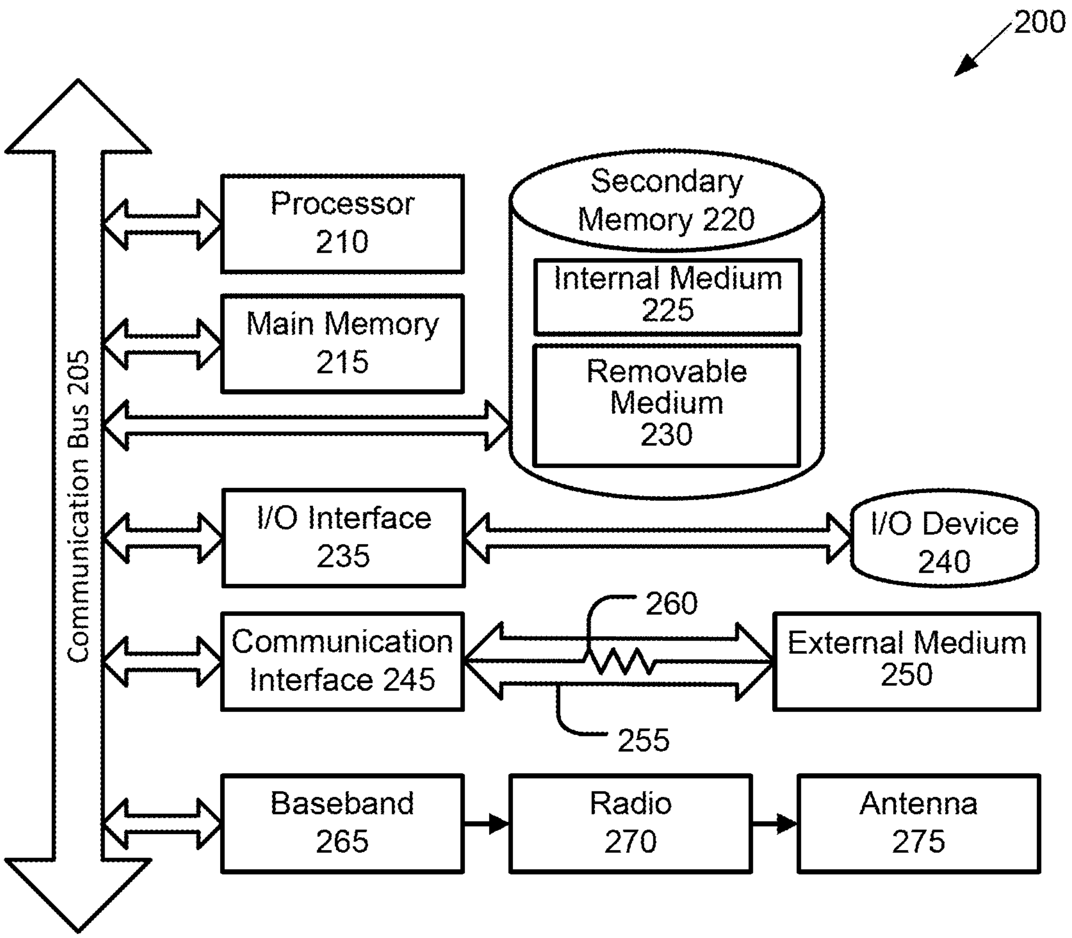
FIG. 2 illustrates an example processing system, by which one or more of the processes described herein may be executed, according to an embodiment.

FIG. 2 is a block diagram illustrating an example wired or wireless system 200 that may be used in connection with various embodiments described herein. For example, system 200 may be used as or in conjunction with one or more of the functions, processes, or methods (e.g., to store and/or execute the application or one or more software modules of the application) described herein, and may represent components of platform 110, user system(s) 130, external system (s) 140, and/or other processing devices described herein. System 200 can be a smartphone device, a tablet computer, or any other processor-enabled device that is capable of wired or wireless data communication and preferable capable of data communication on a WIFI network and also on a cellular network. Other computer systems and/or architectures may be also used, as will be clear to those skilled in the art.

System 200 preferably includes one or more processors, such as processor 210. Additional processors may be provided, such as an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. Such auxiliary processors may be discrete processors or may be integrated with processor 210. Examples of processors which may be used with system 200 include, without limitation, the Pentium® processor, Core i7® processor, and Xeon® processor, all of which are available from Intel Corporation of Santa Clara, California.

Processor 210 is preferably connected to a communication bus 205. Communication bus 205 may include a data channel for facilitating information transfer between storage and other peripheral components of system 200. Furthermore, communication bus 205 may provide a set of signals used for communication with processor 210, including a data bus, address bus, and/or control bus (not shown). Communication bus 205 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and/or the like.

System 200 preferably includes a main memory 215 and may also include a secondary memory 220. Main memory 215 provides storage of instructions and data for programs executing on processor 210, such as one or more of the functions and/or modules discussed herein. It should be understood that programs stored in the memory and executed by processor 210 may be written and/or compiled according to any suitable language, including without limitation C/C++, Java, JavaScript, Perl, Visual Basic, .NET, and the like. Main memory 215 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 220 may optionally include an internal medium 225 and/or a removable medium 230. Removable medium 230 is read from and/or written to in any well-known manner. Removable storage medium 230 may be, for example, a magnetic tape drive, a compact disc (CD) drive, a digital versatile disc (DVD) drive, other optical drive, a flash memory drive, and/or the like.

Secondary memory 220 is a non-transitory computer-readable medium having computer-executable code (e.g., disclosed software modules) and/or other data stored thereon. The computer software or data stored on secondary memory 220 is read into main memory 215 for execution by processor 210.

In alternative embodiments, secondary memory 220 may include other similar means for allowing computer programs or other data or instructions to be loaded into system 200. Such means may include, for example, a communication interface 245, which allows software and data to be transferred from external storage medium 250 to system 200. Examples of external storage medium 250 may include an external hard disk drive, an external optical drive, an external magneto-optical drive, and/or the like. Other examples of secondary memory 220 may include semiconductor-based memory, such as programmable read-only memory (PROM), erasable programmable read-only memory (EPROM), electrically erasable read-only memory (EEPROM), and flash memory (block-oriented memory similar to EEPROM).

As mentioned above, system 200 may include a communication interface 245. Communication interface 245 allows software and data to be transferred between system 200 and external devices (e.g. printers), networks, or other information sources. For example, computer software or executable code may be transferred to system 200 from a network server (e.g., platform 110) via communication interface 245. Examples of communication interface 245 include a built-in network adapter, network interface card (NIC), Personal Computer Memory Card International Association (PCMCIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 200 with a network (e.g., network(s) 120) or another computing device. Communication interface 245 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 245 are generally in the form of electrical communication signals 260. These signals 260 may be provided to communication interface 245 via a communication channel 255. In an embodiment, communication channel 255 may be a wired or wireless network (e.g., network(s) 120), or any variety of other communication links. Communication channel 255 carries signals 260 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed application, or software modules) is stored in main memory 215 and/or secondary memory 220. Computer programs can also be received via communication interface 245 and stored in main memory 215 and/or secondary memory 220. Such computer programs, when executed, enable system 200 to perform the various functions of the disclosed embodiments as described elsewhere herein.

In this description, the term "computer-readable medium" is used to refer to any non-transitory computer-readable storage media used to provide computer-executable code and/or other data to or within system 200. Examples of such media include main memory 215, secondary memory 220 (including internal memory 225, removable medium 230, and external storage medium 250), and any peripheral device communicatively coupled with communication interface 245 (including a network information server or other network device). These non-transitory computer-readable media are means for providing executable code, programming instructions, software, and/or other data to system 200.

In an embodiment that is implemented using software, the software may be stored on a computer-readable medium and loaded into system 200 by way of removable medium 230, I/O interface 235, or communication interface 245. In such an embodiment, the software is loaded into system 200 in the form of electrical communication signals 260. The software, when executed by processor 210, preferably causes processor 210 to perform one or more of the processes and functions described elsewhere herein.

In an embodiment, I/O interface 235 provides an interface between one or more components of system 200 and one or more input and/or output devices 240. Example input devices include, without limitation, sensors, cameras, microphones, keyboards, touch screens or other touch-sensitive devices, biometric sensing devices, computer mice, trackballs, pen-based pointing devices, and/or the like. Examples of output devices include, without limitation, other processing devices, speakers, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), head mounted displays (HMDs), and/or the like. In some cases, an input and output device 240 may be combined, such as in the case of a touch panel display (e.g., in a smartphone, tablet, or other mobile device).

In an embodiment, the I/O device 240 may be any type of external or integrated display and may include one or more discrete displays that in aggregate form the I/O device 240. The I/O device 240 may be capable of 2D or 3D presentation of visual information to a user of the system 200. In one embodiment, the I/O device 240 may be a virtual reality or augmented reality device in the form of HMD by the user so the user may visualize the presentation of information in 3D.

System 200 may also include optional wireless communication components that facilitate wireless communication over a voice network and/or a data network (e.g., in the case of user system 130). The wireless communication components comprise an antenna system 275, a radio system 270, and a baseband system 265. In system 200, radio frequency (RF) signals are transmitted and received over the air by antenna system 275 under the management of radio system 270.

In an embodiment, antenna system 275 may comprise one or more antennae and one or more multiplexors (not shown) that perform a switching function to provide antenna system 275 with transmit and receive signal paths. In the receive path, received RF signals can be coupled from a multiplexor to a low noise amplifier (not shown) that amplifies the received RF signal and sends the amplified signal to radio system 270.

In an alternative embodiment, radio system 270 may comprise one or more radios that are configured to communicate over various frequencies. In an embodiment, radio system 270 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 270 to baseband system 265.

If the received signal contains audio information, then baseband system 265 decodes the signal and converts it to an analog signal. Then the signal is amplified and sent to a speaker. Baseband system 265 also receives analog audio signals from a microphone. These analog audio signals are converted to digital signals and encoded by baseband system 265. Baseband system 265 also encodes the digital signals for transmission and generates a baseband transmit audio signal that is routed to the modulator portion of radio system 270. The modulator mixes the baseband transmit audio signal with an RF carrier signal, generating an RF transmit signal that is routed to antenna system 275 and may pass through a power amplifier (not shown). The power amplifier amplifies the RF transmit signal and routes it to antenna system 275, where the signal is switched to the antenna port for transmission.

Baseband system 265 is also communicatively coupled with processor 210, which may be a central processing unit (CPU). Processor 210 has access to data storage areas 215 and 220. Processor 210 is preferably configured to execute instructions (i.e., computer programs, such as the disclosed application, or software modules) that can be stored in main memory 215 or secondary memory 220. Computer programs can also be received from baseband processor 260 and stored in main memory 210 or in secondary memory 220, or executed upon receipt. Such computer programs, when executed, enable system 200 to perform the various functions of the disclosed embodiments.

Figure 3:
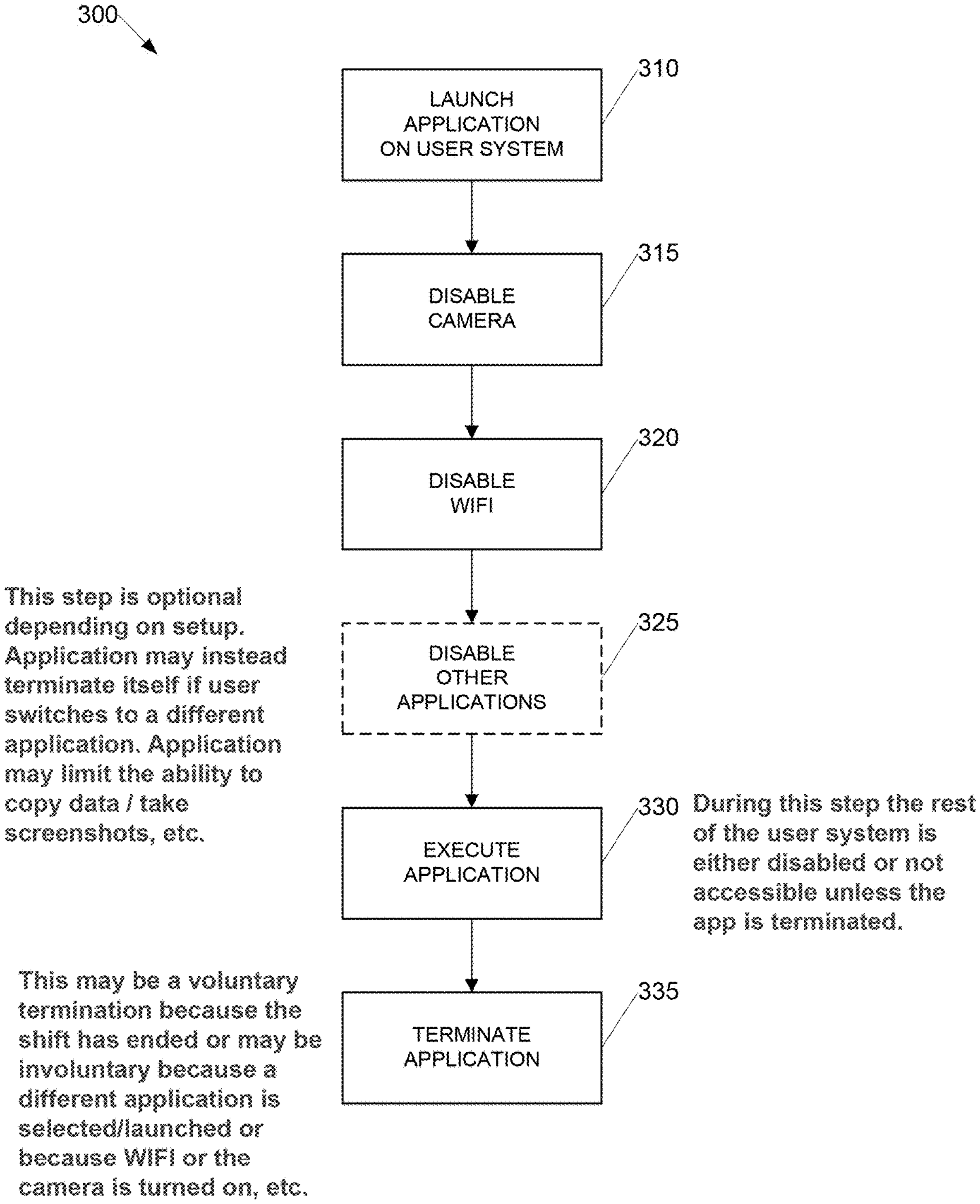
FIG. 3 illustrates an example process for queue management, according to an embodiment.

FIG. 3 illustrates an example process 300 for queue management, according to an embodiment. In one aspect, the process 300 may be carried out by the system described with respect to FIG. 1 in combination with one of more processing devices described with respect to FIG. 2. Initially, at 310 the user system launches the queue management application. For example, the application could be application 132 previously described with respect to FIG. 1. In one aspect, the user system may be a wireless communication device such as a smart phone.

Next, at 315, the queue management application disables the camera and at 320 the queue management application disables the WIFI. In one aspect, disabling the camera and WIFI curtail the ability of the user system, outside of the queue management application, to capture image data and/or communicate via a local WIFI network. Advantageously, once the camera and WIFI capabilities are disabled, the user system is at less risk for misuse and at less risk for data leaks.

Next, at 325 the queue management application optionally disables all other non-critical applications. Disabling all non-critical applications advantageously reduces the risk that the user system is misused and reduces the risk of data on the user system being compromised.

Next, at 330 the user system executes the queue management application to process requests and provide discount information for use in commercial transactions for prescription drug purchases. In one aspect, while the queue management application is executing, the queue management application may be configured to monitor the state of the user system to confirm that the queue management application maintains the sole focus and if a user of the user system switches to a different application, the queue management application terminates itself and removes any queue management application data from memory. Additionally, the queue management application may also be configured to terminate itself if the user system receives a command to capture an image of the screen when the queue management application is presenting sensitive information on the screen of the user system. Advantageously, this results in the rest of the user system being effectively disabled or inaccessible while the queue management application is executing.

Next, at 335 the queue management application is terminated. The termination may be because the application is no longer needed, e.g., at the end of a work day or the end of a work shift. Alternatively, the termination may be because a user attempted to capture data or capture a screen image including data or switch to a different application. Additionally, the termination may be because the disabled WIFI was turned on or the disabled camera was turned on.

Figure 4:
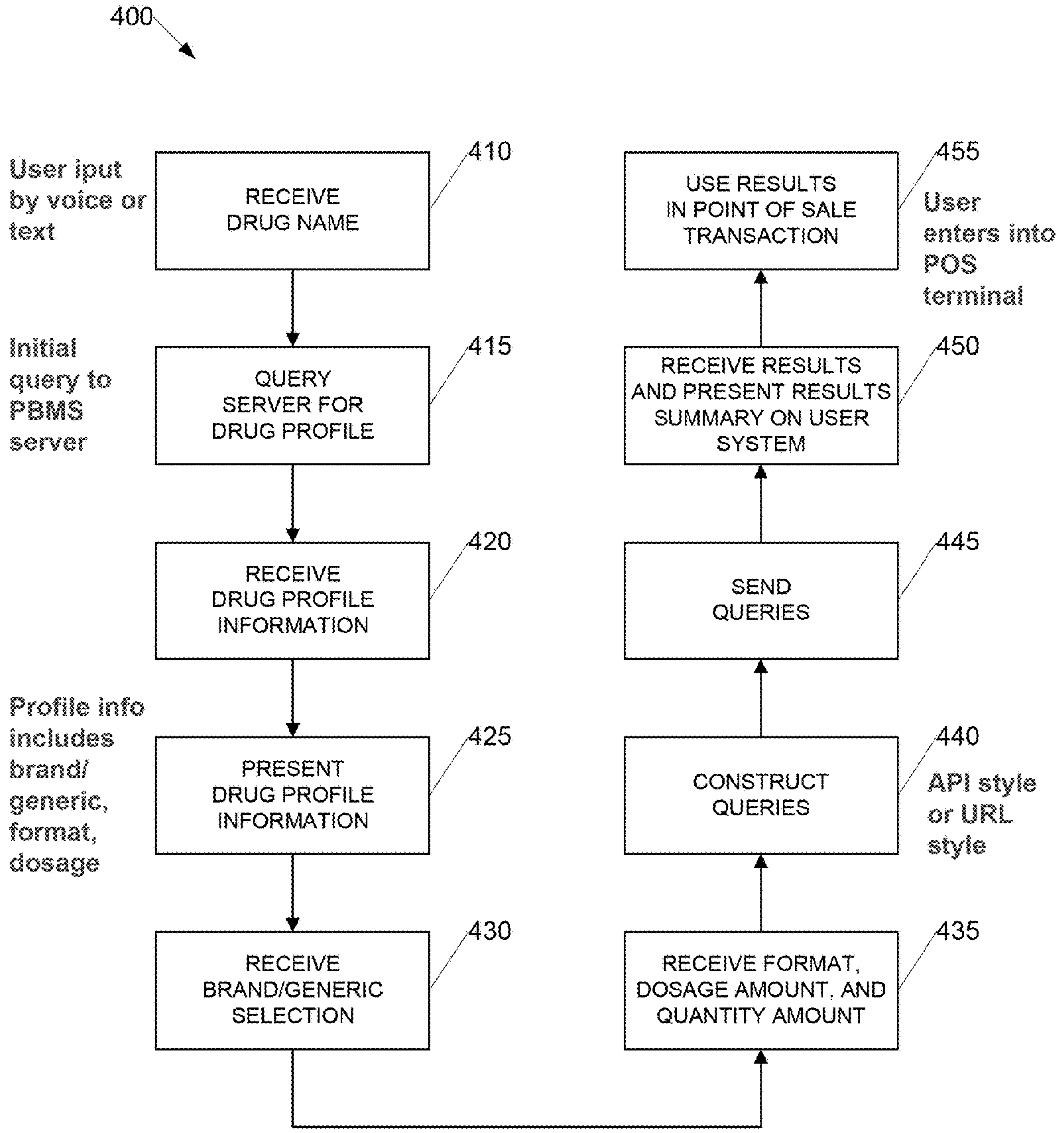
FIG. 4 illustrates an example process for applying a discount to a commercial transaction, according to an embodiment.

FIG. 4 illustrates an example process 400 for applying a discount to a commercial transaction, according to an embodiment. In one aspect, the process 400 may be carried out by the system described with respect to FIG. 1 in combination with one of more processing devices described with respect to FIG. 2. Initially, at 410 the queue management application receives a user input include the name of a product to be purchased, for example a prescription drug. The user input may be received as voice data via a microphone on the user device or as text input into a field of a user interface presented on a display of the user device.

Next at 415, the application constructs and sends a query to an external system requesting information about the product to be purchased. In one aspect, the query is sent to a pharmacy benefits manager (PBM) company server.

Next, at 420, the application receives product information in response to the query. For example, the PBM server may send drug profile information that provides information about the drug to be purchased. Such information may include one or more brand names for the drug and one or more generic names for the drug. The drug profile information may also include the format of the drug for example, tablet, gel cap, liquid, or cream, just to name a few. The drug profile information may also include the and a list of common dosages for the drug and a list of the common amounts/quantify of the drug that correlates to the different formats and/or dosages for the drug.

Next at 425, the application presents the drug profile information via a user interface designed to allow a user of the application to select the desired characteristics of the drug to be purchased.

Next, at 430, the application receives a selection of the brand name or generic name of the drug to be purchased. Once the drug name selection is received, at 435 the application receives additional information related to the purchase of the drug, including the format of the drug, the dosage amount, and the quantity. In one aspect, each selection received by the application may reduce the number of choices for one or more subsequent selections to made by the user of the application. For example, if a generic drug name is selected, the format of the drug may be limited to tablets only while if a brand drug name is selected, the form of the drug may include both tablets and gelcaps.

Next at 440, once the application has received at least the minimum amount of information needed to construct a query to a pharmacy discount service, the application constructs one or more queries to be sent to one or more pharmacy discount services. Each individual query may be formatted according to a defined application programming interface (API) or may be formatted according to a defines uniform resource locator (URL). Advantageously, the system may construct the one or more queries in parallel so that they may be used in parallel.

At 445, the one or more queries are sent by the application to one or more pharmacy discount service servers, where the queries may be processed in parallel. Such parallel processing of queries significantly reduces the overall transaction time for the commercial transaction in which the drug is purchased with a discount from one of the many pharmacy discount service providers. In one aspect, when the WIFI of the user system that is executing the application is disabled, the application sends the queries to the pharmacy discount service servers via a cellular network.

Next, at 450 the application receives a response to each of the queries sent to each of the many pharmacy discount service providers. The application analyzes the responses and constructs a summary of the responses to the queries. The summary of the responses is then presented by the application on a display of the user device. In one aspect, the summary of the responses may be presented as an ordered list based on the amount of the discount that is offered by each pharmacy discount service.

Next, at 455, the results of one of the discounts offered by one of the pharmacy discount services is used in the point of sale transaction when the drug is purchased. For example, the results advantageously include certain key information for the prescription drug purchase that includes the BIN, the PCN, the Group, and the MemberID/UserID. This information is advantageously provided when the summary is presented so that the information may be easily used in the commercial transaction.

In one aspect, the key information may be typed into the point of sale device as part of the commercial transaction. Alternatively, the key information may be provided to the point of sale device by way of direct user device to point of sale device Bluetooth® communication. Alternatively, the key information may be provided to the point of sale device by way of presenting a bar code or a QR code to an image sensor (e.g., bar code reader or camera) of the POS device such that the POS device conducts a lookup for the key information.

In one aspect, constructing the queries in parallel and sending the queries for processing in parallel by the many pharmacy discount service providers and constructing a summary of the results that is ordered by the amount of the discount that is offered significantly reduces the time for the commercial transaction to purchase the prescription drug. By significantly reducing the time for each commercial transaction to purchase a prescription drug, the system improves the operation of the point of sale device that processes the commercial transaction and significantly improves throughput at the drive through window or the register (or both) at the location where the prescription drugs are being purchased.

Figure 5:
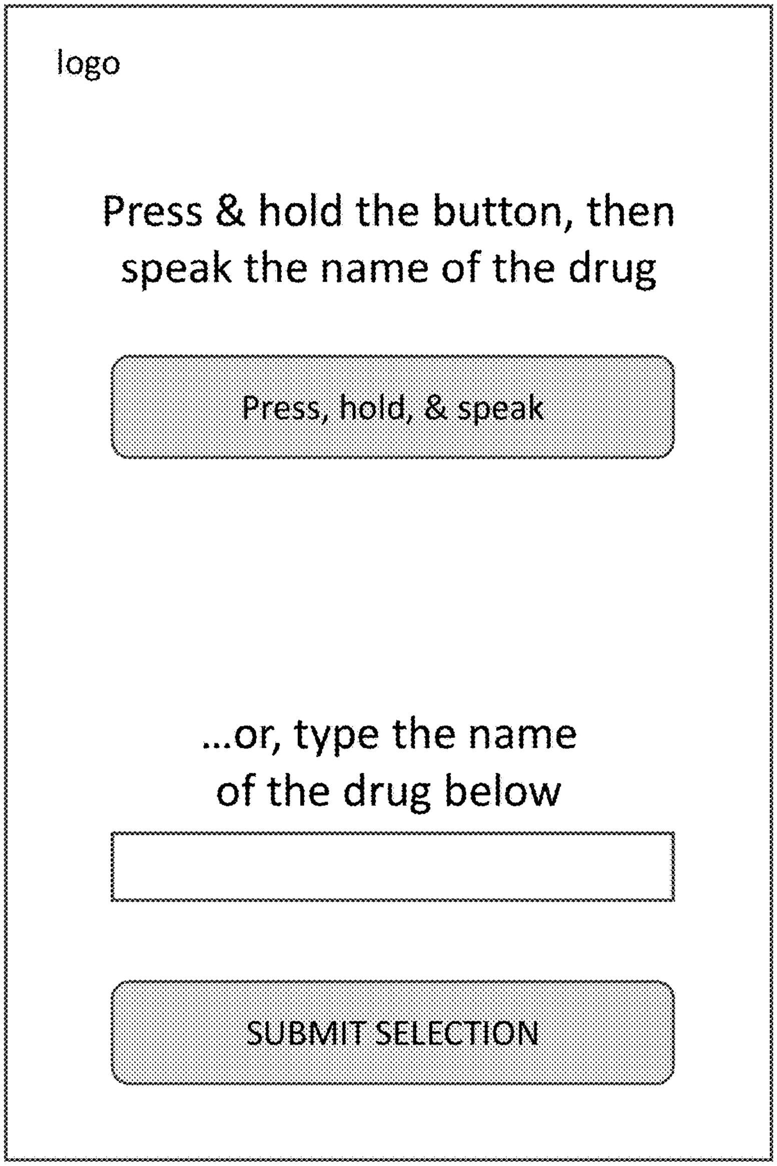
FIG. 5 illustrates an example mobile device input screen for identifying an item to be purchased in a commercial transaction, according to an embodiment of the invention.

FIG. 5 illustrates an example mobile device input screen 500 for identifying an item to be purchased in a commercial transaction, according to an embodiment of the invention. In the illustrated embodiment, a user of the application may input the name of the product being purchased using a voice input capability of the application or the user may input the name of the product using a text input capability of the application.

Figure 6:
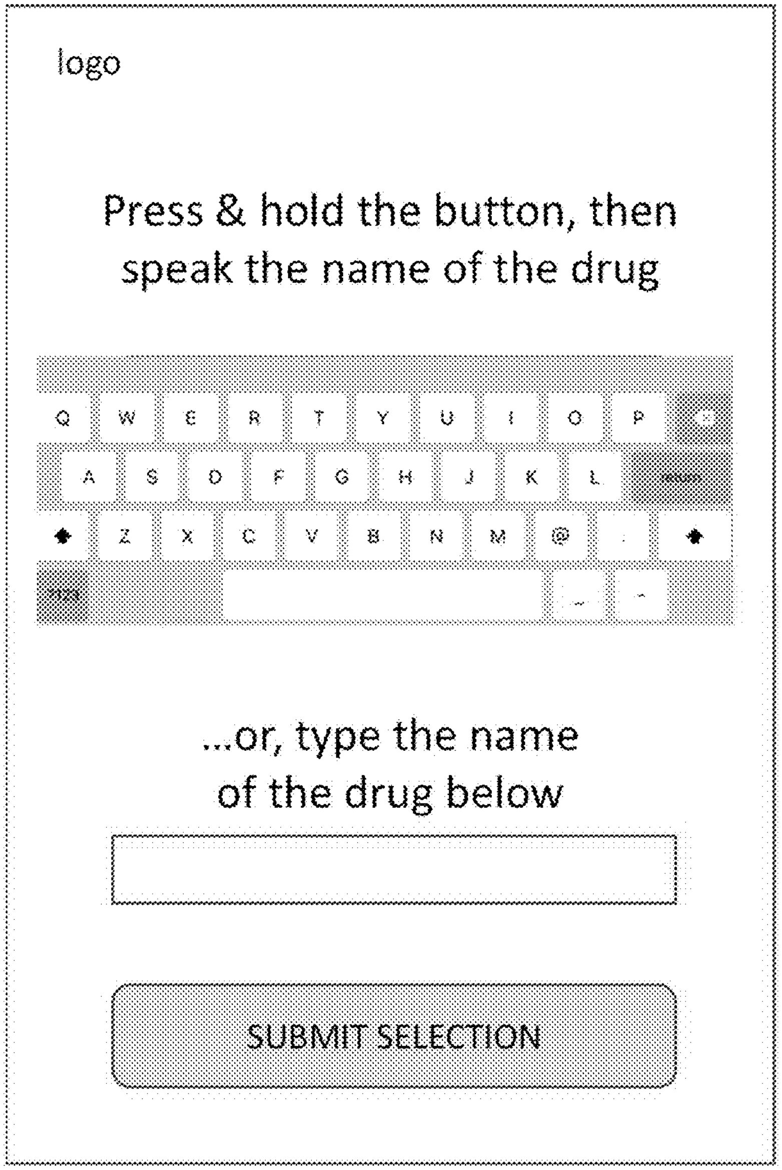
FIG. 6 illustrates an alternative example mobile device input screen for identifying an item to be purchased in a commercial transaction, according to an embodiment of the invention.

FIG. 6 illustrates an alternative example mobile device input screen 600 for identifying an item to be purchased in a commercial transaction, according to an embodiment of the invention. In the illustrated embodiment, a user has selected a text input capability and in response to that selection, the application is configured to present a keyboard that can be used to input the text.

Figure 7:
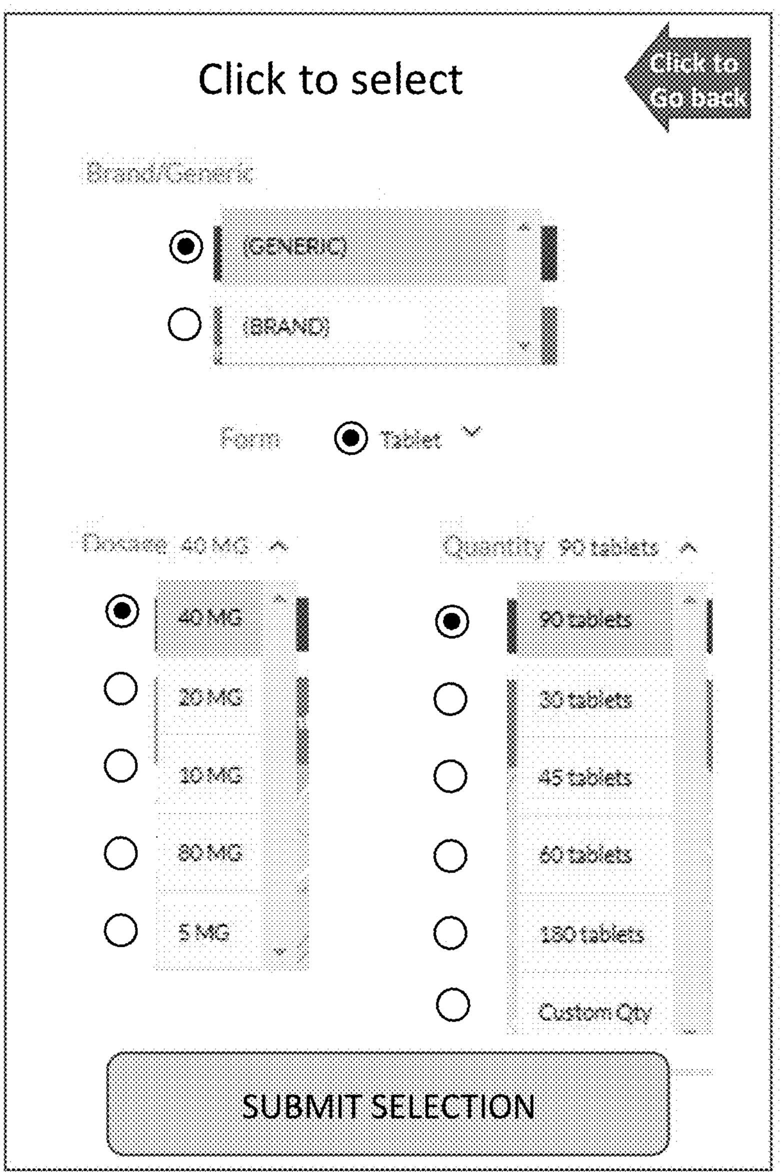
FIG. 7 illustrates an example mobile device input screen for identifying characteristics of an item to be purchased in a commercial transaction, according to an embodiment of the invention.

FIG. 7 illustrates an example mobile device input screen 700 for identifying characteristics of an item to be purchased in a commercial transaction, according to an embodiment of the invention. In the illustrated embodiment, selections for certain characteristics of the product to be purchased are presented. For example, various brand names and generic names may be presented so that one can be selected. In one aspect, the selection may be made by a radio button feature. Additionally, various forms of the drug may also be presented for selection, for example by way of a drop-down list feature. Additionally, various dosage options for the drug may also be presented for selection, for example by way of a radio button feature. Additionally, various quantify options for the drug may also be presented for selection, for example by way of a radio button feature.

In one aspect, the application may be configured to only allow selection of one characteristic at a time. Advantageously, sequential selection may simplify the downstream information that is presented for subsequent selection when a prior selection constrains the options for a subsequent selection.

Additionally, in one aspect, the minimum characteristics that are selected for a prescription drug to be purchased include the drug name, the format, the dosage, and the quantity.

Once the selections for the various characteristics have been received, the application may activate the submit selection button so that all of the selected characteristics for the drug to be purchased may be submitted for use in constructing one or more queries to one or more pharmacy discount service providers.

Figure 8:
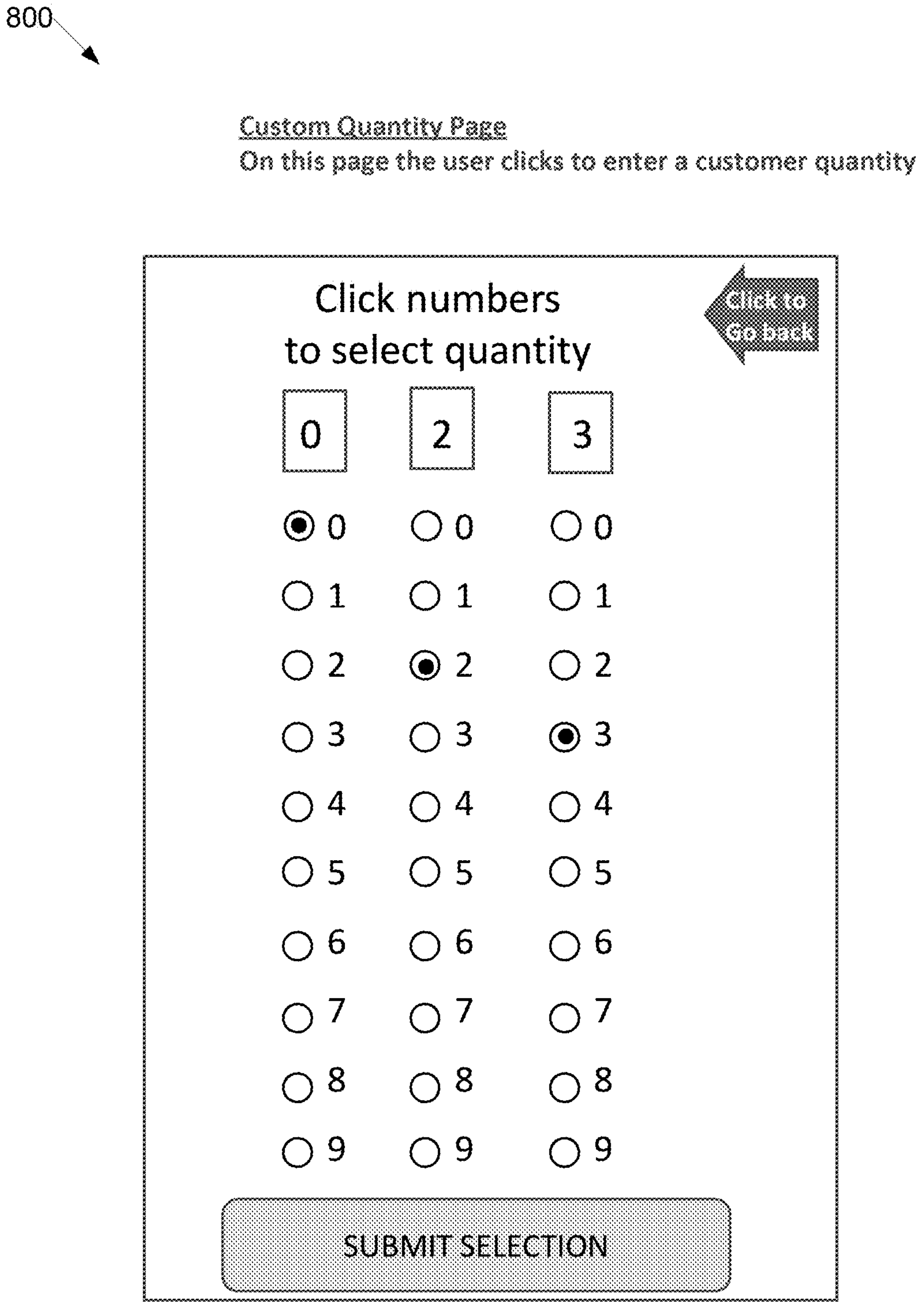
FIG. 8 illustrates an alternative example mobile device input screen for identifying characteristics of an item to be purchased in a commercial transaction, according to an embodiment of the invention.

FIG. 8 illustrates an alternative example mobile device input screen 800 for identifying characteristics of an item to be purchased in a commercial transaction, according to an embodiment of the invention. For example, when a customized quantity of a prescription drug has been prescribed or is desired, the application may allow a user to input a customized quantity, for example by individual selecting each digit in a three digit number. This may be accomplished, for example by way of a radio button feature for each of the three digits as shown.

Figure 9:
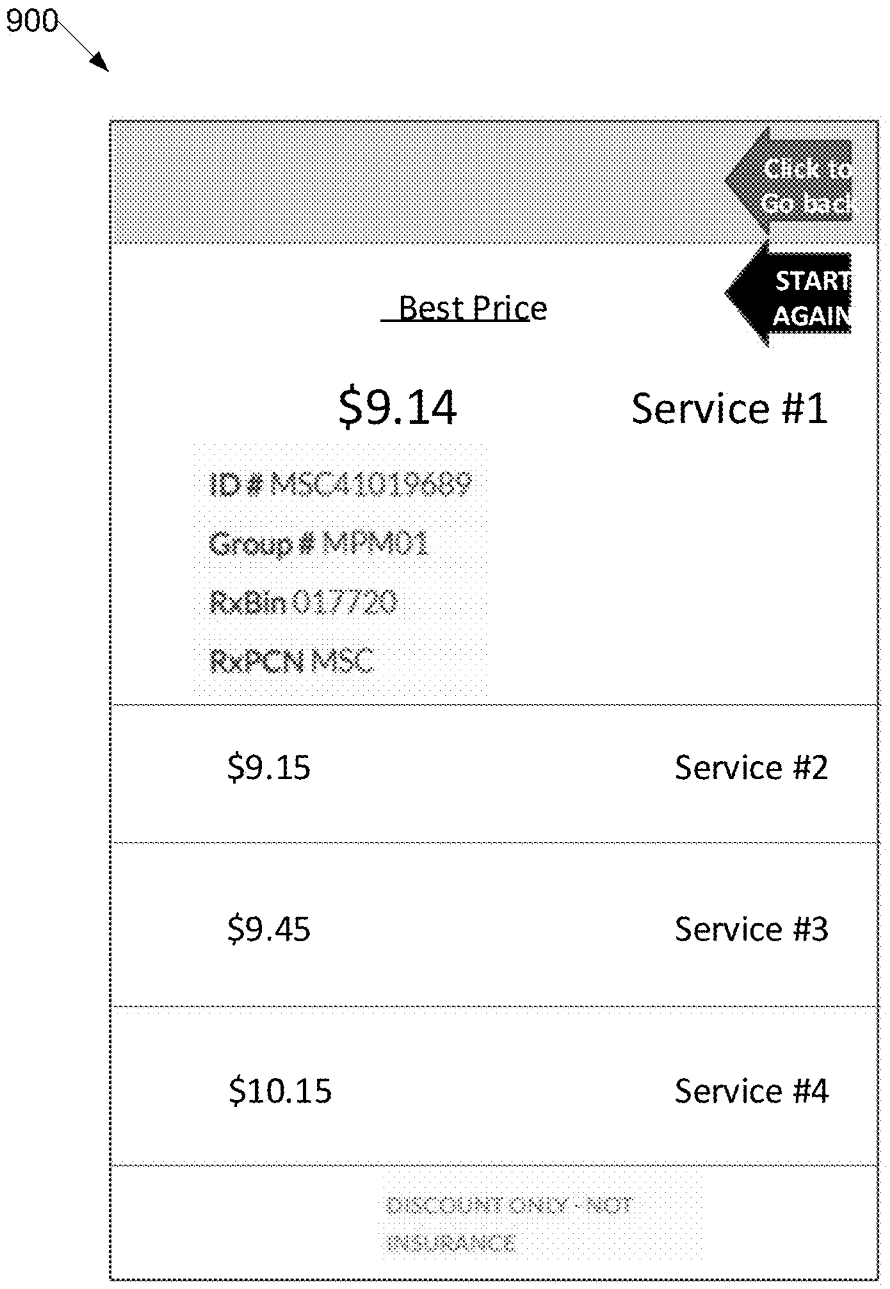
FIG. 9 illustrates an example mobile device screen for providing a summary of available discounts for an item to be purchased in a commercial transaction, according to an embodiment of the invention.

FIG. 9 illustrates an example mobile device screen 900 for providing a summary of available discounts for an item to be purchased in a commercial transaction, according to an embodiment of the invention. In the illustrated embodiment, the summary of the results of the plurality of individual queries is sorted by the best price, or alternatively the best discount. The summary also includes the name of each pharmacy discount service provider that was queried and that provided a response the corresponding price (or alternatively, the corresponding discount) for each pharmacy discount service provider. In an aspect where the summary list is sorted by the best price, certain key information is also provided to simplify the anticipated transaction to purchase the prescription drug using the discount from the particular pharmacy discount service provider. Specifically, that key information includes the BIN, the PCN, the Group, and the MemberID or user ID.

In one aspect, if a pharmacy discount service provider further down the list is selected, the first pharmacy discount service provider in the list may collapse to obscure the key information while the selected pharmacy discount service provider in the list may expand to show the key information.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A system for increasing queue throughput, the system comprising:

a user system located in a pharmacy, the user system comprising:

a cellular network communication system configured for data communication via a cellular network;

a WIFI communication system configured for data communication via a data communication network; and a camera system configured to capture digital images and store digital images in a memory;

a user interface configured to receive first information corresponding to a prescription drug purchase and obtain profile information from a pharmacy benefits manager service, the profile information corresponding to the prescription drug and comprising a plurality of first data elements including at least one of a brand name, a generic name, a drug form, one or more dosage amounts, and one or more quantity amounts; and a processor configured to control the cellular network communication system to carry out data communication over the cellular network and to control the user interface to receive the first information and obtain the profile information, wherein the processor of the user system is further configured to, initiate an execution state of a queue management application, in response to initiating the execution state, selectively restrict access to hardware resources associated with (i) the WIFI communication system and (ii) the camera system, thereby enforcing exclusive access by the queue management application to a cellular network communication interface during the execution state, wherein enforcing exclusive cellular communication and restricting access to the WIFI communication system enables parallel processing of the plurality of queries via the cellular network; and during the execution state and subsequent to restricting access to the WIFI communication system and the camera system, generate a plurality of queries, each query comprising at least a portion of the profile information, control the cellular network communication system to route each of the plurality of queries exclusively through the cellular network communication system while preventing transmission via an alternate network interface, receive a response to each of the plurality of queries via the cellular network, each response including second information comprising a plurality of second data elements including at least a discount price indicator from the respective pharmacy discount service for the prescription drug at the pharmacy, monitor the execution state of the queue management application;

upon detection of (i) a request to switch to a different application or (ii) a request to capture an image, automatically terminate the queue management application and remove associated data from memory to prevent access to queue management application data outside the execution state; and a point of sale platform located in the pharmacy, the point of sale platform comprising:

a data communication system configured for data communication via a data communication network separate from the cellular network;

a processor configured to control the data communication system to carry out data communication over the data communication network;

wherein the processor of the point of sale platform is further configured to receive third information corresponding to the prescription drug purchase and communicate with one or more external platforms via the data communication network to consummate a sale of the prescription drug, wherein the processor of the point of sale platform is further configured to provide at least a portion of the third information to the one or more external platforms in connection with the sale of the prescription drug, wherein the third information includes at least one of the first data elements and at least one of the second data elements.

2. An apparatus for increasing queue throughput, comprising:

a cellular network communication system configured for data communication via a cellular network;

a non-transitory computer readable medium configured to store executable programmed modules;

a user interface configured to receive first information corresponding to a prescription drug purchase and present second information including at least a discount price indicator for the prescription drug purchase;

a processor communicatively coupled with the non-transitory computer readable medium and configured to execute programmed modules stored in the non-transitory computer readable medium, the processor further configured to control the cellular network communication system to carry out data communication over the cellular network and to control the user interface to receive the first information and provide the second information;

wherein the processor is further configured to, initiate an execution state of a queue management application, in response to initiating the execution state, selectively restrict access to hardware resources associated with (i) WIFI functions of the apparatus and (ii) camera functions of the apparatus, thereby enforcing exclusive access by the queue management application to a cellular network communication interface during the execution state, wherein enforcing exclusive cellular communication and restricting access to WIFI functions enables parallel processing of the plurality of queries via the cellular network; and during the execution state and subsequent to restricting access to WIFI and camera functions of the apparatus, control the user interface to obtain profile information from a pharmacy benefits manager service, the profile information corresponding to the prescription drug and comprising a plurality of first data elements including at least one of a brand name, a generic name, a drug form, one or more dosage amounts, and one or more quantity amounts;

generate a plurality of queries, each query comprising at least a portion of the profile information, route each of the plurality of queries to one of a plurality of pharmacy discount services exclusively via the cellular network while preventing routing via an alternate network interface, receive a response to each of the plurality of queries via the cellular network, each response including second information comprising a plurality of second data elements including at least a discount price indicator for the prescription drug;

sort the responses to each of the plurality of queries by discount price indicators;

control the user interface to present a sorted list of responses to each of the plurality of queries;

monitor the execution state of the queue management application; and upon detection of (i) a request to switch to a different application or (ii) a request to capture an image, automatically terminate the queue management application and remove associated data from memory to prevent access to queue management application data outside the execution state.

3. A method for increasing queue throughput performed by a processor-enabled device, where one or more processors of the processor-enabled device are programmed to perform steps comprising:

initiate an execution state of a queue management application;

in response to initiating the execution state, selectively restrict access to hardware resources associated with (i) WIFI functions of the processor-enabled device and (ii) camera functions of the processor-enabled device, thereby enforcing exclusive access by the queue management application to a cellular network communication interface during the execution state, wherein enforcing exclusive cellular communication and restricting access to WIFI functions enables parallel processing of the plurality of queries via a cellular network; and during the execution state and subsequent to restricting access to the WIFI and camera functions of the processor-enabled device, control a user interface to obtain profile information from a pharmacy benefits manager service, the profile information corresponding to a prescription drug and comprising a plurality of first data elements including at least one of a brand name of the prescription drug, a generic name of the prescription drug, a delivery form of the prescription drug, one or more dosage amounts of the prescription drug, and one or more quantity amounts of the prescription drug;

generate a plurality of queries, each query comprising at least a portion of the profile information;

route each of the plurality of queries to one of a plurality of pharmacy discount services exclusively via the cellular network while preventing routing via an alternate network interface;

receive a response to each of the plurality of queries via the cellular network while preventing routing via an alternate network interface, each response including second information comprising a plurality of second data elements including at least a discount price indicator for the prescription drug;

sort the responses to each of the plurality of queries based on the discount price indicators;

control the user interface to present a sorted list of responses to each of the plurality of queries;

monitor the execution state of the queue management application; and upon detection of (i) a request to switch to a different application or (ii) a request to capture an image, automatically terminate the queue management application and remove associated data from memory to prevent access to queue management application data outside the execution state.

4. A system comprising at least one processor communicatively coupled with at least one non-transitory computer readable medium, wherein the processor is programmed to:

control a user interface to obtain profile information from a pharmacy benefits manager service, the profile information corresponding to a prescription drug and comprising a plurality of first data elements including at least one of a brand name of the prescription drug, a generic name of the prescription drug, a delivery form of the prescription drug, one or more dosage amounts of the prescription drug, and one or more quantity amounts of the prescription drug;

generate a plurality of queries, each query comprising at least a portion of the profile information;

initiate an execution state of a queue management application;

in response to initiating the execution state, selectively restrict access to hardware resources associated with (i) WIFI functions and (ii) camera functions, thereby enforcing exclusive access by the queue management application to a cellular network communication interface during the execution state, wherein enforcing exclusive cellular communication and restricting access to WIFI functions enables parallel processing of the plurality of queries via a cellular network; and during the execution state and subsequent to restricting access to all WIFI and camera functions, route each of the plurality of queries to one of a plurality of pharmacy discount services exclusively via the cellular network while preventing routing via an alternate network interface;

receive a response to each of the plurality of queries via the cellular network, each response including second information comprising a plurality of second data elements including at least a discount price indicator for the prescription drug;

sort the responses to each of the plurality of queries based on the discount price indicators; and control the user interface to present a sorted list of responses to each of the plurality of queries, wherein the processor is further programmed to monitor the execution state of the queue management application and upon detection of (i) a request to switch to a different application or (ii) a request to capture an image, automatically terminate the queue management application and remove from memory data corresponding to the application to prevent access to queue management application data outside the execution state.

5. The system of claim 1, wherein the processor of the user system is further configured to disable one or more other applications before generating the plurality of queries.

6. The system of claim 1, wherein the user interface of the user system is further configured to receive the first information as voice data via a microphone.

7. The system of claim 1, wherein the processor of the user system is further configured to control the user interface of the user system to present a sorted list of responses to each of the plurality of queries, wherein a single response in the sorted list comprises information required for a prescription drug purchase transaction.

8. The apparatus of claim 2, wherein the processor is further configured to disable one or more other applications before generating the plurality of queries.

9. The apparatus of claim 2, wherein the processor is further configured to receive the first information as voice data via a microphone.

10. The apparatus of claim 2, wherein a single response in the sorted list comprises information required for a prescription drug purchase transaction.

11. The method of claim 3, wherein the steps further comprise disabling one or more other applications before generating the plurality of queries.

12. The method of claim 3, wherein the steps further comprise receiving the first information as voice data via a microphone.

13. The method of claim 3, wherein a single response in the sorted list comprises information required for a prescription drug purchase transaction.

14. The system of claim 4, wherein the processor is further configured to disable one or more other applications before generating the plurality of queries.

15. The system of claim 4, wherein the processor is further configured to receive the first information as voice data via a microphone.

16. The system of claim 4, wherein a single response in the sorted list comprises information required for a prescription drug purchase transaction.

17. The system of claim 1, wherein the processor of the user system is further configured to monitor a state of the user system and terminate an application controlling the user interface and remove from memory data corresponding to the application upon occurrence of one of: a request to switch the user system to a different application, and a request to capture an image of a screen of the user system.

18. The apparatus of claim 2, wherein the processor is further configured to monitor a state of the apparatus and terminate an application controlling the user interface and remove from memory data corresponding to the application upon occurrence of one of: a request to switch the apparatus to a different application, and a request to capture an image of a screen of the apparatus.

19. The method of claim 3, wherein the one or more processors of the processor-enabled device are further configured to monitor a state of the processor-enabled device and terminate an application controlling the user interface and remove from memory data corresponding to the application upon occurrence of one of: a request to switch the processor-enabled device to a different application, and a request to capture an image of a screen of the processor-enabled device.

* * * * *